United States Patent [19]

Takematsu et al.

[11] Patent Number: 4,551,169

[45] Date of Patent: Nov. 5, 1985

[54] METAMETHOXY ARYL CARBAMATE DERIVATIVES AND HERBICIDES

[75] Inventors: Tetsuo Takematsu; Makoto Konnai; Hideo Morinaka, all of Utsunomiya; Yunji Nonaka; Akira Nakanishi, both of Shinnanyo, all of Japan

[73] Assignee: Toyo Soda Manufacturing Company, Limited, Shinnanoyo, Japan

[21] Appl. No.: 476,313

[22] Filed: Mar. 17, 1983

[30] Foreign Application Priority Data

Mar. 17, 1982 [JP] Japan .................................. 57-40759
Jul. 16, 1982 [JP] Japan .................................. 57-122921
Sep. 7, 1982 [JP] Japan .................................. 57-154596

[51] Int. Cl.$^4$ ................ C07D 213/75; C07C 125/067; A01N 47/20; A01N 47/22
[52] U.S. Cl. .......................................... 71/94; 71/111; 546/297; 560/29; 564/74
[58] Field of Search .................... 546/297; 560/29; 564/74; 71/94, 111

[56] References Cited

U.S. PATENT DOCUMENTS 3,334,126 8/1967 Miyazaki et al. .................. 260/455
4,021,224 5/1977 Pallos et al. ........................ 71/94

FOREIGN PATENT DOCUMENTS 4210859 6/1942 Japan .
4210860 6/1942 Japan .
5016411 5/1975 Japan .

OTHER PUBLICATIONS

Derwent Abstract 10859/67 "Preparation of Carbamates" (1967).
Derwent Abstract 10860/67 "Preparation of Carbamates" (1967).
Derwent Abstract 47008w/28 Fungicidal, Nematicidal, And Plant Growth Regulating Composition (1975).

Primary Examiner—Henry R. Jiles
Assistant Examiner—Dale A. Bjorkman
Attorney, Agent, or Firm—Oblon, Fisher, Spivak, McClelland & Maier

[57] ABSTRACT

Carbamate derivatives having the formula:

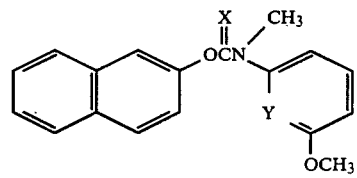

wherein X represents an oxygen atom or a sulfur atom and Y represents a —CH— group or a nitrogen atom; and herbicides utilizing the same.

4 Claims, No Drawings

METAMETHOXY ARYL CARBAMATE DERIVATIVES AND HERBICIDES

DETAILED EXPLANATION OF THE INVENTION

This invention relates to carbamate derivatives, a process for producing them and herbicides containing the compounds as an effective component.

Hitherto, it has been well known that carbamate compounds have herbicidal activity and also that arylthiocarbamate compounds exhibit antifungal activity and nematocidal activity. However, naphthyl carbamates have not been known as effective herbicides. There is a description in Japanese examined patent publication Nos. 10859/1967 and 10860/1967 that 2-naphthyl-N-aryl-N-methyl carbamates do not exhibit herbicidal activity.

Although there is a description in Japanese examined patent publication No. 16411/1975 that 2-naphthyl N-phenylcarbamate exhibits growth controlling action on rice plants and radishes to give the rice plants excellent increase in the fresh weight, there is no description suggesting that these carbamate derivatives exhibit herbicidal activity.

The present inventors have keenly conducted an investigation to develop naphthyl carbamate derivatives which exhibit sufficient herbicidal activity and further selective characteristics, and have found that specified naphthyl carbamates show no phytotoxity on transplanted rice plants but selective herbicidal activity. This finding lead to accomplish this invention.

That is to say, this invention provides carbamate derivatives having the general formula (I):

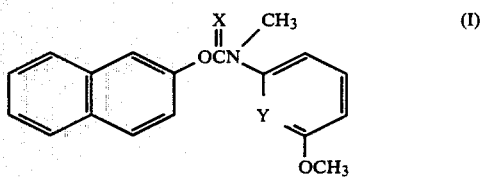

wherein X represents an oxygen atom or a sulfur atom and Y represents CH group or a nitrogen atom, a process for producing thereof and herbicides containing these compounds.

The compounds represented by the above-stated general formula (I) (hereinafter referred to as the compounds of this invention) are novel compounds which have not been described in any literature.

Herbicides containing the compounds of this invention show an extremely excellent herbicidal activity, especially against barnyard grass in a flooded paddy field and also herbicides containing thiocarbamate derivatives of the compounds of this invention have the same activity against general weeds of paddy fields. In addition, the herbicides of this invention are substantially harmless against transplanted rice plants and preferable as herbicides for use in paddy fields. Furthermore, one of the compounds of this invention shows excellent herbicidal selectivity between weeds belonging to the true grass family and broadleaved crops in the treatment for farmland soil. Therefore, this compound is recognized to have an applicability in herbicides used in farmlands.

The carbamate derivatives of this invention which are represented by the general formula (I) can be produced pursuant to the following reaction equations:

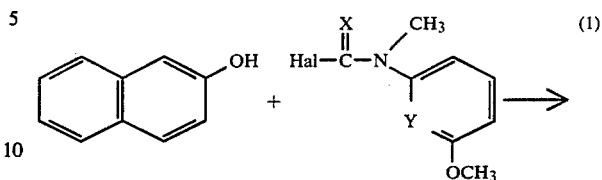

General Formula (I)

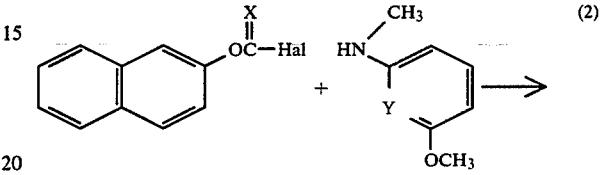

General Formula (I)

wherein X represents an oxygen atom or a sulfur atom, Y represents CH group or a nitrogen atom, and Hal represents halogen atoms.

The above-stated reactions proceed in the presence of dehydrohalogenation agents and further in the presence or absence of reaction solvents usually at reaction temperature ranging from 0° C. to 150° C., during a reaction time of about few minutes to 48 hours.

As the dehydrohalogenation agents, alkali hydroxides such as sodium hydroxide, potassium hydroxide and the like; alkali earth hydroxides such as calcium hydroxide and the like; alkali carbonates such as sodium carbonate, potassium carbonate, sodium bicarbonate, potassium bicarbonate and the like; metal hydrides such as sodium hydride and the like; and tertiary amines such as triethylamine, N,N-dimethylaniline, pyridine and the like can be exemplified. The starting amine derivatives can be used as the dehydrohalogenation agents in the reaction shown by the equation (2).

As the reaction solvents, water; alcohols such as methanol, ethanol, isopropanol and the like; ketones such as acetone, methyl ethyl ketone and the like; aromatic hydrocarbons such as benzene, toluene, xylene and the like; ethers such as ethyl ether, tetrahydrofuran, dioxane and the like; halogenated hydrocarbons such as chlorobenzene, chloroform, carbon tetrachloride, dichloroethane and the like; polar solvents such as dimethylformamide, dimethylsulfoxide and the like can be used.

The process for producing the compounds is explained herein-below in detail.

EXAMPLE 1

[Preparation of O-2-naphthyl N-(3-methoxyphenyl)-N-methylthiocarbamate (Compound No.2)]

2.00 g of N-(3-methoxyphenyl)-N-methylthiocarbamoyl chloride, 1.44 g of β-naphthol and 1.66 g of anhydrous potassium carbonate were added to 50 ml of methyl ethyl ketone and heated to reflux for 15 hours. The reaction mixture was poured into water after it was cooled to room temperature and the products were extracted with benzene. The benzene solution was subsequently washed with water and aqueous saturated sodium chloride solution and then benzene was removed by distillation under reduced pressure after drying over anhydrous Magnesium sulfate. The residue was purified by the column chromatography (eluted with benzene on a silica gel) to give 1.45 g of O-2-naphthyl N-(3-methoxyphenyl)-N-methylthiocarbamate in crystals (Yield: 45%). A part of the crystals was recrystallized from ethanol. Colorless crystals having melting point of 93° to 94° C. were obtained.

EXAMPLE 2

[Preparation of O-2-naphthyl N-(6-methoxy-2-pyridyl)-N-methylthiocarbamate (Compound No. 4)]

1.38 g of 2-methoxy-6-methylaminopyridine and 1.38 g of anhydrous potassium carbonate were added to 20 ml of acetone, to which 2.23 g of 2-naphthyl chlorothioformate dissolved in 20 ml of acetone was added at room temperature under stirring. The stirring was continued for 30 minutes under the same conditions and then the mixture was heated to reflux for 2 hours. The reaction mixture was poured into water after it was cooled to room temperature and the products were extracted with benzene. The benzene solution was subsequently washed with water and aqueous saturated sodium chloride solution and then benzene was removed by distillation under reduced pressure after drying over anhydrous magnesium sulfate. The residue was purified by the column chromatography (eluted with benzene on a silica gel) to give 2.75 g of O-2-naphthyl N-(6-methoxy-2-pyridyl)-N-methylthiocarbamate (Yield: 85%). A part of the product was recrystallized from acetone-hexane. Colorless crystals having melting point of 95.5° to 97° C. were obtained.

The compounds of this invention are listed in Table 1 together with their physical properties and elemental analysis.

hexanone, N,N-dimethylformamide, mineral oil and the like are used.

Furthermore, surface-active agents and stabilizers can be added when they are required. In addition, the herbicides of this invention can be applied after incorporating them with other agricultural chemicals used in the same field, for example, insecticides, fungicides, herbicides, growth controlling agents or fertilizers. Especially, there are occasions where it is proper to incorporate the present herbicides with another herbicide for the purpose of reducing labor required for spreading or for the purpose of extending the spectrum of weed species which can be effectively prevented.

As the additional herbicide, triazine herbicides such as Atrazine, Simazine, Simetryn, Prometryn and the like; carbamate homologue herbicides such as Asulam, Benthiocarb, Molinate and the like; urea herbicides such as Linuron, Dymrone, and the like; phenoxy-series herbicides such as 2,4-D, MCP, MCPB, Naproanilide and the like; diphenyl ether herbicides such as Nitrofen, Chlornitrofen, Chlomethoxynil and the like; heterocyclic-series herbicides such as Oxadiazon, Pyrazolate, Bentazon and the like; and amide homologue herbicides such as Alachlor, Butachlor, Propanil and the like can be exemplified. It is possible to provide mixtures of the compounds of this invention which are effective to many grass species by being skillfully combined with one or more than two of these herbicides.

Examples of formulation in which the compounds of this invention were used are described hereinbelow. In the Examples the term "parts" means parts by weight.

EXAMPLE 3

[Water dispersible powder]

10 Parts of compound No. 1 of this invention were

TABLE 1

| Compounds of this Invention | | | Melting Point (°C.) | IR Spectrum Characteristic Absorption (cm$^{-1}$, KBr) | NMR Spectrum ($\delta$ = ppm, CDCL$_3$) | Elemental analysis (%) Found value (Calculated value) | | |
|---|---|---|---|---|---|---|---|---|
| No. | X | Y | | | | C | H | N |
| 1 | O | CH | 61.5~62.3 | 1720 | 3.30(3H, s) | 73.98 | 5.53 | 4.63 |
| | | | | 1595 | 3.56(3H, s) | (74.25) | (5.57) | (4.55) |
| | | | | 1485 | 6.53~7.90(11H, m) | | | |
| | | | | 1350 | (CCl$_4$) | | | |
| 2 | S | CH | 93~94 | 1595 | 3.66(3H, s) | 70.25 | 5.39 | 4.72 |
| | | | | 1583 | 3.73(3H, s) | (70.57) | (5.30) | (4.33) |
| | | | | 1465 | 6.66~7.90(11H, m) | | | |
| | | | | 1425 | | | | |
| | | | | 1360 | | | | |
| 3 | O | N | 140.5~142 | 1720 | 3.61(3H, s) | 69.83 | 5.21 | 9.13 |
| | | | | 1580 | 3.91(3H, s) | (70.11) | (5.23) | (9.09) |
| | | | | 1460 | 6.36~6.66(1H, m) | | | |
| | | | | 1405 | 7.17~8.00(9H, m) | | | |
| | | | | 1350 | | | | |
| 4 | S | N | 95.5~97 | 1600 | 3.75(3H, s) | 66.42 | 4.89 | 8.81 |
| | | | | 1455 | 3.92(3H, s) | (66.65) | (4.97) | (8.64) |
| | | | | 1415 | 6.63(1H, d) | | | |
| | | | | 1365 | 6.90~7.95(9H, m) | | | |

In order to use the compounds of this invention, a proper amount of one or two compounds represented by the above-stated general formula (I) is incorporated with an inert carrier to use as usual agricultural chemicals like water dispersible powder, emulsifiable concentrate granules and so on.

As solid carriers, talc, clay, diatomaceous earth, bentonite and the like are exemplified. As liquid carriers, water, alcohol, benzene, kerosine, cyclohexane, cycloadmixed and pulverized together with 87.3 part of Zeeklite (Trade name, manufactured by Kunimine Kogyo Co., Ltd.) used as the carrier material, 1.35 parts of Neopelex (Trade name, Manufactured by Kao Atlas Co., Ltd.) and 1.35 parts of Sorpol 800A (Trade name, manufactured by Toho Kagaku Kogyo Co., Ltd.) to give 10% water dispersible powder.

EXAMPLE 4

[Emulsifiable concentrate]

25 Parts of compound No. 2 of this invention were admixed and dissolved together with 65 parts of benzene and 10 parts of Solpol 800A to give 25% emulsifiable concentrate.

EXAMPLE 5

[Granules]

After 10 parts of compound No. 4 of this invention, 50 parts of bentonite, 35 parts of Kunilite (Trade name, manufactured by Kokuho Kogyo Co., Ltd.) and 5 parts of Sorpol 800A used as the surface-active agent were admixed and pulverized. After 10 parts of water was added, the mixture was kneaded to give a homogeneous mixture. The mixture was then extruded through sieving perforations having diameter of 0.7 mm and dried. The product was cut off to give 10% granules having length of 1-2 mm.

As to the herbicidal action of the compounds of this invention, characteristic features are in that it intensively exert such action on grasses at the time of the germination and strongly suppress the growth after the germination. Therefore, the residual activity is extremely long-lasting in weed bodies. That is to say, these compounds kill weeds, or inhibit the growth or considerably suppress the growth to result in a failure of the growth competition against crops.

The compounds of this invention are appropriate as an active ingredient of herbicides for use in a treatment of flooded paddy field before the germination of weeds. They are used in the amount of 10 to 1,000 g/10 ares, preferably 100 to 500 g/10 ares as an active ingredient.

The compounds of this invention are highly safe to young seedling of rice plants and no affection has been observed even in an application amount of 1000 g/10 ares as an active ingredient. Therefore these compounds have extremely excellent characteristics as herbicides for paddy fields.

As to compound No. 4 of this invention, it has a excellent herbicidal activity against barnyard grass even in a growth period (2- to 3-leaf stage). Accordingly it is a characteristic feature of this compound that it's applicable period is considerably extended. That is to say, it is shown that it has high applicability as a soil-applied herbicide in a cultivation of transplanted rice plants in the primary to medium stage and also as a soil-applied herbicide used immediately after flooding in a cultivation of dry seeded rice.

Furthermore, it is shown that the No. 4 compound of this invention has high applicability as a herbicide used in farmlands, because the compound, when it is used as a soil-applied herbicide after the seeding of general broadleaved crops such as soybean, effectively prevent true grass family weeds such as barnyard grass, crab grass and foxtail, and purple nutsedge.

The herbicidal effects of the compounds of this invention are explained in the below-stated Examples.

EXAMPLE 6

[Test for the Herbicidal Effects under Submerged Conditions (1)]

Paddy field soil was charged in porcelain pots having a diameter of 9 cm, and then water was added. After the soil was tilled, seeds of weeds were sown on the surface of the soil and two bunches of rice plants (variety: Nihonbare) being in 2-leaf stage were transplanted in 1 cm depth. The pots were flooded to give water depth of 2 cm on the next day and predetermined amounts of water dispersible powder of the compounds of this invention, which were dispersed in 10 ml of water were added dropwise into every pots on the surface of water for the treatment. Then they were settled in a greenhouse and the herbicidal effects as well as the influence against the rice plants were examined after 3 weeks. Evaluation is expressed by a 6 stage system, details of which are shown below. The obtained results are shown in Table 2.

| Expression | Phytotoxicity against rice plants | Herbicidal Effects |
|---|---|---|
| 5 | Killed | 100% Prevention (Amount of Residual Weeds: 0%) |
| 4 | Considerably injured | 80% Prevention (Amount of Residual Weeds: 20%) |
| 3 | Substantially injured | 60% Prevention (Amount of Residual Weeds: 40%) |
| 2 | A little injured | 40% Prevention (Amount of Residual Weeds: 60%) |
| 1 | Slightly injured | 20% Prevention (Amount of Residual Weeds: 80%) |
| 0 | No injury | 0% Prevention (Amount of Residual Weeds: 100%) |

TABLE 2

| No. of the Compound of this Invention | Dose (g/10 ares) | Phytotoxicity against rice plant Transplanted rice plant | Herbicidal Effects barnyard grass | umbrella plant | bulrush | monochoria | Rotala indica |
|---|---|---|---|---|---|---|---|
| 1 | 125 | 0 | 4 | 0 | 0 | 1 | 2 |
|   | 250 | 0 | 5 | 2 | 0 | 1 | 2 |
|   | 500 | 0 | 5 | 3 | 1 | 2 | 3 |
|   | 1000 | 0 | 5 | 3 | 1 | 3 | 4 |
| 2 | 125 | 0 | 5 | 5 | 3 | 5 | 5 |
|   | 250 | 0 | 5 | 5 | 4 | 5 | 5 |
|   | 500 | 0 | 5 | 5 | 5 | 5 | 5 |
|   | 1000 | 0 | 5 | 5 | 5 | 5 | 5 |
| 3 | 125 | 0 | 4 | 5 | 0 | 0 | 0 |
|   | 250 | 0 | 5 | 5 | 0 | 1 | 0 |
|   | 500 | 0 | 5 | 5 | 1 | 1 | 1 |
|   | 1000 | 0 | 5 | 5 | 2 | 2 | 1 |
| 4 | 125 | 0 | 5 | 5 | 5 | 5 | 5 |
|   | 250 | 0 | 5 | 5 | 5 | 5 | 5 |
|   | 500 | 0 | 5 | 5 | 5 | 5 | 5 |
|   | 1000 | 0 | 5 | 5 | 5 | 5 | 5 |

TABLE 2-continued

| No. of the Compound of this Invention | Dose (g/10 ares) | Phytotoxicity against rice plant Transplanted rice plant | Herbicidal Effects | | | | |
|---|---|---|---|---|---|---|---|
| | | | barnyard grass | umbrella plant | bulrush | monochoria | *Rotala indica* |
| Benthiocarb (Reference Agent) | 125 | 1 | 5 | 5 | 2 | 2 | 3 |
| | 250 | 2 | 5 | 5 | 2 | 2 | 3 |
| | 500 | 2 | 5 | 5 | 3 | 3 | 4 |
| | 1000 | 3 | 5 | 5 | 5 | 4 | 5 |
| Not Treated | 0 | 0 | 0 | 0 | 0 | 0 | 0 |

EXAMPLE 7

[Test for the Herbicidal Effects under Submerged Conditions (2)]

Paddy field soil was charged in porcelain pot having a diameter of 9 cm, and then water was added. After the soil was tilled, seeds of barnyard grass were sown on the surface of the soil and two bunches of rice plants (variety: Nihonbare) being in 2-leaf stage were transplanted in 1 cm depth. Flooding was carried out to give water depth of 2 cm on the next day. Predetermined amounts of water dispersible powder of the compound No. 4 of this invention, which was dispersed in 10 ml of water, was added dropwise into every pots on the surface of water for the treatment before the germination of and at the time of the 2-leaf stage (10 days after the seeding) of barnyard grass. The examination was carried out after 3 weeks from the treatment with the chemicals and results were evaluated in the similar manner as in EXAMPLE 6. Results are shown in Table 3.

TABLE 3

| No. of the Compound of this Invention | Dose (g/10 ares) | Phytotoxicity against rice plant Transplanted rice plant | Herbicidal Effects against Barnyard grass | |
|---|---|---|---|---|
| | | | pre-germination | 2-leaf stage |
| No. 4 | 12.5 | 0 | 5 | 5 |
| | 25 | 0 | 5 | 5 |
| | 50 | 0 | 5 | 5 |
| | 100 | 0 | 5 | 5 |
| Benthiocarb (Reference Agent) | 12.5 | 0 | 2 | 1 |
| | 25 | 0 | 3 | 2 |
| | 50 | 0 | 4 | 2.5 |
| | 100 | 1 | 5 | 4 |
| Not Treated | 0 | 0 | 0 | 0 |

EXAMPLE 8

[Test for the Herbicidal Effects by the Surface Treatment of Farmland Soil]

Farmland soil was charged into porcelain pots having a diameter of 12 cm and several kinds of plant seeds were sown. The soil is further covered by the soil in 1 cm thickness. Predetermined amounts of water dispersible powder of the compound No. 4 of this invention, which was dispersed in with 10 ml of water per every pots, was sprayed on the soil surface for the treatment. The pots were stationarily placed in a greenhouse and received sprayed water in proper time intervals. After 3 weeks from the treatment with the chemicals, the herbicidal effects and influences against soybean and cotton plants were examined in the similar manner as in EXAMPLE 6. Results are shown in Table 4.

TABLE 4

| No. of the Compound of this Invention | Dose (g/10 ares) | Phytotoxicity | | Herbicidal Effects | | |
|---|---|---|---|---|---|---|
| | | Soybean plant | Cotton plant | Barnyard grass | Crab grass | Foxtail |
| No. 4 | 50 | 0 | 0 | 4.5 | 5 | 4.5 |
| | 100 | 0 | 0 | 5 | 5 | 5 |
| | 200 | 0 | 0 | 5 | 5 | 5 |
| | 400 | 0 | 0 | 5 | 5 | 5 |
| Benthiocarb (Reference Agent) | 50 | 0 | 0 | 3 | 4 | 3 |
| | 100 | 0 | 0 | 4 | 5 | 4 |
| | 200 | 0 | 0 | 5 | 5 | 5 |
| | 400 | 0 | 0 | 5 | 5 | 5 |
| Not Treated | 0 | 0 | 0 | 0 | 0 | 0 |

EXAMPLE 9

Test for the Herbicidal effects by the Admixture Treatment with Farmland Soil]

Farmland soil was charged into porcelain pots having a diameter of 12 cm to the half way of the depth. On the soil additional farmland soil admixed with predetermined amounts of water dispersible powder of the compound No. 4 of this invention, which was dispersed in 10 ml of water, was charged to give a further 3 cm thickness. Seeds of soybean and cotton plants and germinated tubers of purple nutsedge were planted in the pots in 1.5 cm depth from the soil surface. They were settled in a greenhouse and received sprayed water in proper time intervals. After 4 weeks from the treatment with the chemicals, the herbicidal effects and influences against soybean and cotton plants were examined. The evaluation was carried out in the similar manner as in EXAMPLE 6. Results are shown in Table 5.

TABLE 5

| No. of the Compound of this Invention | Dose (g/10 ares) | Phytotoxicity | | Herbicidal Effects Purple nutsedge |
|---|---|---|---|---|
| | | Soybean plant | Cotton plant | |
| No. 4 | 50 | 0 | 0 | 1 |
| | 100 | 0 | 0 | 2 |
| | 200 | 0 | 0 | 4 |
| | 400 | 0 | 0 | 4.5 |
| Benthiocarb (Reference Agent) | 50 | 0 | 0 | 0 |
| | 100 | 0 | 0 | 1 |
| | 200 | 0 | 0 | 2 |
| | 400 | 0 | 0 | 3 |
| Not Treated | 0 | 0 | 0 | 0 |

We claim:

1. Carbamate derivatives represented by the formula (I);

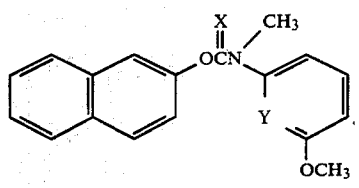

wherein X represents an oxygen atom or a sulfur atom and Y represents CH group or a nitrogen atom.

2. O-2-naphthyl N-(3-methoxyphenyl)-N-methylthiocarbamate, as recited in claim 1.

3. O-2-naphthyl N-(6-methoxy-2-pyridyl)-N-methylthiocarbamate, as recited in claim 1.

4. A herbicidal composition comprising an effective amount of one or more compounds of the formula (I):

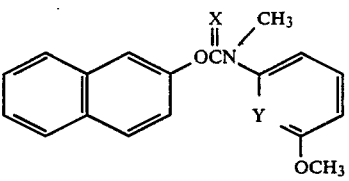

wherein X represents an oxygen atom or sulfur atom and Y represents a —CH— group or nitrogen atom.

* * * * *

UNITED STATES PATENT AND TRADEMARK OFFICE
CERTIFICATE OF CORRECTION

PATENT NO. : 4,551,169

DATED : November 5, 1985

INVENTOR(S) : Tetsuo Takematsu, et al.

It is certified that error appears in the above-identified patent and that said Letters Patent is hereby corrected as shown below:

-- The Applicants information is incorrect and should read as follows:

4th inventor Yuji Nonaka, Shinnanyo, JAPAN --

Signed and Sealed this

Twenty-fourth Day of June 1986

[SEAL]

Attest:

DONALD J. QUIGG

Attesting Officer

Commissioner of Patents and Trademarks